(12) United States Patent
Anderson et al.

(10) Patent No.: US 7,713,211 B2
(45) Date of Patent: May 11, 2010

(54) METHOD OF OPTIMIZING PATIENT OUTCOME FROM EXTERNAL COUNTERPULSATION THERAPY

(75) Inventors: Stephen T. Anderson, North Oaks, MN (US); Dean J. MacCarter, Englewood, CO (US)

(73) Assignee: Shape Medical Systems, Inc., North Oaks, MN (US)

( * ) Notice: Subject to any disclaimer, the term of this patent is extended or adjusted under 35 U.S.C. 154(b) by 1702 days.

(21) Appl. No.: 10/889,595

(22) Filed: Jul. 12, 2004

(65) Prior Publication Data

US 2004/0254482 A1 Dec. 16, 2004

Related U.S. Application Data

(63) Continuation-in-part of application No. 10/797,943, filed on Mar. 11, 2004, now abandoned.

(60) Provisional application No. 60/453,989, filed on Mar. 12, 2003.

(51) Int. Cl.
  *A61B 5/08* (2006.01)
(52) U.S. Cl. ..................................... 600/484
(58) Field of Classification Search ............... 607/1, 607/2, 9, 17, 18, 20, 23, 24; 600/481, 483–485, 600/508, 513, 526, 529, 531, 532
See application file for complete search history.

(56) References Cited

U.S. PATENT DOCUMENTS

| 4,463,764 | A | * | 8/1984 | Anderson et al. | 600/532 |
| 5,410,472 | A | * | 4/1995 | Anderson | 482/9 |
| 6,174,289 | B1 | * | 1/2001 | Binder | 600/532 |
| 2003/0208106 | A1 | * | 11/2003 | Anderson et al. | 600/300 |
| 2003/0233061 | A1 | * | 12/2003 | Hui | 601/152 |

* cited by examiner

*Primary Examiner*—Mark W Bockelman
*Assistant Examiner*—Roland Dinga
(74) *Attorney, Agent, or Firm*—Nikolai & Mersereau, P.A.; C. G. Mersereau

(57) ABSTRACT

A method of data management for optimizing the patient outcome from the provision of external counterpulsation (ECP) therapy is described. This method describes a process by which sets of dynamic cardiopulmonary dependent variables are measured during steady-state conditions, displayed, and translated into quantitative and qualitative measurements while the independent variables of ECP, cuff inflation duration and cuff inflation pressure settings of ECP systems, are altered by a physician. In combination with visual observation and computer-assisted ranking of the dependent variables, a physician can utilize the resulting information to render decisions on the optimal choice of the independent variables. The method will enable physicians to collect, view, track and manage complicated data using well-understood visualization techniques to better understand the consequences, acutely and chronically, of their therapeutic actions in general, and of their provision of ECP therapy in particular.

14 Claims, 9 Drawing Sheets

FIG.4

|  | Cuff Inflation Pressure | Cuff Inflation Duration |
|---|---|---|
| Minimum | (60) 150 | (66) 350 |
| Average | (62) 195 | (68) 400 |
| Maximum | (64) 240 | (70) 450 |

FIG. 5

| Elapsed Time | System Operator Tasks | Data Processing Tasks |
|---|---|---|
| 0 | Comed Operator CPX | |
| 1 | Start ECP Therapy<br>Prestart Measurement<br>Set CID min<br>Start Measurment | Display Variables |
| 25 | Observe Variables<br>Set CID ave | Display Variables<br>Store Variables to CID min |
| 4 | Obcerve Variables<br>Set CID max | Display Variables<br>Store Variables to CID ave |
| 55 | Observe Variables | Display Vvariables<br>Store Variables to CID max |
| 65 | Select and Sed CID opt<br>Set CIP ave | Calculate Decision Matrix<br>Print Selection Report |
| 8 | Observe Variables<br>Set CIP ave | Display Variables<br>Store Variables to CIP min |
| 95 | Observe Variables<br>Set CIP max | Display Variables<br>Store Variables to CIP ave |
| 11 | Observe Variables | Display Variables<br>Store to CIP max |
| 12 | Stop Measurement<br>Select and Set CIP opt | Calculate Decision Matrix<br>Print Selection Report |

FIG.6

| Elapsed Time | | | O2 Plus | EQ CO2 | ET CO2 | Vent. Ef. Slope |
|---|---|---|---|---|---|---|
| Start | | | | | | |
| 1 min | Breath 1 | CDI min | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 25 min | Breath 1 | CID ave | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 4 min | Breath 1 | CID max | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 55 min | | | | | | |
| | | | | | | |
| 65 min | Breath 1 | CIP min | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 8 min | Breath 1 | CIP ave | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 95 min | Breath 1 | CIP max | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 11 min | | | | | | |

| | EQ CO2 | | | ET CO2 | | | O2 Plus | | | V.E. Slope | | | Average Totals | | |
|---|---|---|---|---|---|---|---|---|---|---|---|---|---|---|---|
| | Rank | D% | S% | Rank | D% | S% | Rank | D% | S% | Rank | D% | S% | Rank | D% | S% |
| CD min | 75 | 12 | 5 | 75 | 14 | 8 | 100 | 4 | 6 | 50 | 9 | 6 | 75 | 97.5 | 6.2 |
| CD ave | 100 | 0 | 0 | 100 | 8 | 0 | 75 | 12 | 0 | 100 | 16 | 0 | 98.75 | 9 | 0 |
| CD max | 50 | 4 | 10 | 50 | 8 | 16 | 50 | 7 | 2 | 75 | 11 | 2 | 56.25 | 7.5 | 8 |
| | | | | | | | | | | | | | | | |
| CP min | 0 | 0 | 0 | 0 | 0 | 0 | 0 | 0 | 0 | 0 | 0 | 0 | | | |
| CP ave | 0 | 0 | 0 | 0 | 0 | 0 | 0 | 0 | 0 | 0 | 0 | 0 | | | |
| CIP max | 0 | 0 | 0 | 0 | 0 | 0 | 0 | 0 | 0 | 0 | 0 | 0 | | | |

METHOD OF OPTIMIZING PATIENT OUTCOME FROM EXTERNAL COUNTERPULSATION THERAPY

CROSS REFERENCE TO CO-PENDING PROVISIONAL APPLICATION

This application is a Continuation-In-Part of application Ser. No. 10/797,943, filed Mar. 11, 2004, now abandoned which, in turn, claims the benefit of Provisional Application No. 60/453,989, filed Mar. 12, 2003. The entire content of both earlier applications is hereby incorporated by reference in this application.

BACKGROUND OF THE INVENTION

I. Field of the Invention

The present invention relates generally to the field of external counterpulsation therapy (ECP), and more specifically, to a method for optimizing the patient outcome from such therapy. The disclosed method enables physicians to improve the setting of the cuff inflation pressure and the duration of the inflation pulse.

II. Related Art

External counterpulsation (ECP) has been recently FDA approved as a new indication of therapy for the treatment of patients with heart failure (HF) and angina. Although ECP has been shown to improve patient morbidity or their quality of life (QOL), there has been limited success in demonstrating its effect on patient mortality. The ECP technician is required to manually adjust the duration of pressurization of the cuffs located on the patient by observing blood pressure and/or oxygen saturation. The main disadvantage of this technique is that the blood pressure signal is too distal, somewhat distorted, and does not reflect upon kinetic changes in heart and lung function. Cuff pressure is currently fixed—from 220 mmHg to 385 mmHG. The physiologic consequences, in terms of circulation and gas exchange, of using either pressure is poorly understood at present.

DEFINITION OF TERMS

The following contains definitions and explanations of certain terms as used in the present context.

End-Tidal Partial Pressure of $CO_2$ ($PetCO_2$, $ETCO_2$)—The partial pressure of carbon dioxide at the end of expiration, or the highest value of $PCO_2$ during a single expiration.

Forward Pump Function—Refers to the ability of the heart to contract and eject blood which has returned to the heart during its relaxation, or filling, cycle via the aorta against a given amount of resistance, or afterload.

Outcome Measurement: With the individualized set of parameters optimally selected as described, the next step is to make an overall assessment of the patient's risk factors over time. In order to appropriately assess the patient's risk factors that are, in turn, related closely to adverse patient outcomes, the patient must be stressed (normally by mild to moderate exercise) in order to evaluate changes in the sympathetic and parasympathetic components of autonomic balance during dynamic, isotonic exercise and recovery. In other words, a volume load must be placed on the heart in order to assess the cardiopulmonary system's true response to patient activity. It is the same with the assessment of cardiac ischemia using the classical ECG stress test. Some type of exercise modality must be used in order to stress the heart and create an imbalance in myocardial oxygen supply and demand. Unlike the classical ECG stress test, maximal exercise intensity is unnecessary to obtain the measured data. Instead, exercise intensities that reflect those normally experienced by the patient's activities of daily living are used to provide the volume load. Several known predictors of mortality in HF patients are measured during application of the volume load, including ventilatory efficiency slope, oxygen efficiency slope, aerobic power, and the chronotropic response index. Individual and cumulative mortality prediction indices, Kaplan-Meier Plots, and trend graphs are provided to document outcomes status due to supportive therapy with external counterpulsation.

Oxygen Pulse ($O_2$ Pulse)—$O_2$ Pulse is an indirect index of combined cardiopulmonary oxygen transport. It is calculated by dividing oxygen uptake (ml/min) by heart rate. In effect, $O_2$ Pulse is equal to the product of stroke volume and arteriovenous $O_2$ difference. Thus circulatory adjustments that occur during exercise, that is, widening arteriovenous $O_2$ difference, increased cardiac output, and redistribution of blood flow to the working muscle, will increase $O_2$ Pulse. Maximal $O_2$ pulse is higher in fitter subjects, lower in the presence of heart disease, and, more importantly, higher at any given workload in the fitter or healthier individual. On the other hand, $O_2$ Pulse will be reduced in any condition that reduces stroke volume . . . ." V. Froelicher, J. Myers, et al., Exercise and the Heart. Mosby-Year Book, Inc. 1993, p. 38

Retrograde Pump Function—Refers to the filling of the heart during the relaxation part of the cardiac cycle. Filling pressure and the volume of blood that returns to the heart during diastole are termed preload. Any forward pump failure of the heart can increase the preload on the heart to undesirable levels which, in turn, has an adverse retrograde effect on gas exchange in the lung.

Ventilation-Perfusion Coupling—"For gas exchange to be most efficient, there must be a precise match, or coupling, between ventilation (the amount of gas reaching the alveoli) and perfusion (the blood flow in pulmonary capillaries). Changes in the $PCO_2$ within the alveoli cause changes in the diameters of the bronchioles. Passageways servicing areas where alveolar carbon dioxide levels are high dilate, allowing carbon dioxide to be eliminated from the body more rapidly; those servicing areas where the $PCO_2$ is low constrict. As a result of the modifications these two systems (also for $PO_2$), alveolar ventilation and pulmonary perfusion are always synchronized. Poor alveolar ventilation results in low oxygen and high carbon dioxide levels in the alveoli; consequently, the pulmonary capillaries constrict and the airways dilate, bringing airflow and blood flow into closer physiological match. High oxygen and low carbon dioxide alveolar partial pressures cause constriction of the respiratory passageways and a flushing of blood into the pulmonary capillaries. At all times, these homeostatic mechanisms provide the most appropriate conditions for efficient gas exchange." E. Marieb, Human Anatomy and Physiology. Benjamin/Cummings Publishing Company, 1992, p. 749

Ventilatory Efficiency Slope (of Ventilation vs. $VCO_2$)—The recorded test data contain the channels minute ventilation VE and carbon dioxide output $VCO_2$ as time series with sample points (moments of time) $t_i$, so there are two sets of data points $VE_i$ and $VCO_{2i}$ with $i=1, \ldots, N$. To find the best straight line fit $VE = a \, VCO_2 + b$ to the ensemble of point pairs ($VE_i$, $VCO_{2i}$) one can use the linear regression analysis minimizing the sum of squares of distances of these points to a straight line, see for instance PRESS, W. H., B. P. FLANNERY, S. A. TEUKOL- SKY, W. T. VETTERLING; Numerical Recipes, The Art of Scientific Computing. Cambridge University Press, Cambridge etc., 1986, Chapter 14.2. The main results of such an analysis are the constants a and b describing the regression line and the regression coefficient r as a measure for the regularity of data lying along and around this line. The constant a is the VE to $VCO_2$ slope, or ventilatory efficiency slope, of the above mentioned data ensemble.

Ventilatory Equivalent for carbon dioxide ($VE/VCO_2$, $EQCO_2$)—The $EQCO_2$ is calculated by dividing ventilation (L/min) by $VCO_2$ (L/min). "$VE/VCO_2$ represents the ventilatory requirement to eliminate a given amount of $CO_2$ produced by the metabolizing tissues. Since metabolic $CO_2$ is a strong stimulus for ventilation during exercise, VE and $VCO_2$ closely mirror one another, and after a drop in early exercise, $VE/VCO_2$ normally does not increase significantly throughout sub-maximal exercise. However, in the presence of chronic heart failure, $VE/VCO_2$ is shifted upward compared to normals, and high $VE/VCO_2$ values are one of the characteristics of the abnormal ventilatory response to exercise in this condition." Ibid Froehlicher.

SUMMARY OF THE INVENTION

The present invention, to a large extent, obviates the problems discussed in the foregoing for each of the phases described above. The physiology supportive of the present invention involves the relationship of the pulmonary circulation and gas exchange in the lungs that will readily reflect upon ventricular filling pressures, pulmonary venous flow, and ventilation to perfusion matching in the lungs (see also Definitions). A sound physiologic basis exists to support the theory that the oxygen pulse ($O_2$ Pulse), end-expired, partial pressure of $CO_2$ ($ETCO_2$), and ventilatory equivalents of $CO_2$ ($EQCO_2$) are key parameters to assess pump function of the heart and the efficiency of gas exchange in the lungs. Any therapy, which reduces stroke output of the heart, may cause a volume load on the heart, thus affecting the pulmonary venous blood flow gradient and ventilation to perfusion matching in the lungs. When ventilation to perfusion is mismatched, the $ETCO_2$ and $O_2$ Pulse will be reduced and $EQCO_2$ will be increased. Because gas exchange measurements are made on a "breath-by-breath" basis, physiologic changes resulting from altering cuff duration and cuff pressure setting are observable more or less instantaneously, thus they can be used to guide the decision making process in either case.

The individualized programmed set of parameters will differ for each patient, reflecting the fact that each patient has unique cardiac and pulmonary function.

BRIEF DESCRIPTION OF THE DRAWINGS

In the drawings:

FIG. 4 illustrates a Boundary Conditions Table for a particular ECP system;

FIG. 5 illustrates a CID/CIP Optimization Protocol showing when particular tasks occur;

FIG. 6 illustrates the organization of the measured data once it is acquired during the Optimization Protocol;

FIG. 8 illustrates the organization of the Decision Matrix and sample values for the calculated results;

DETAILED DESCRIPTION

Figure 1:
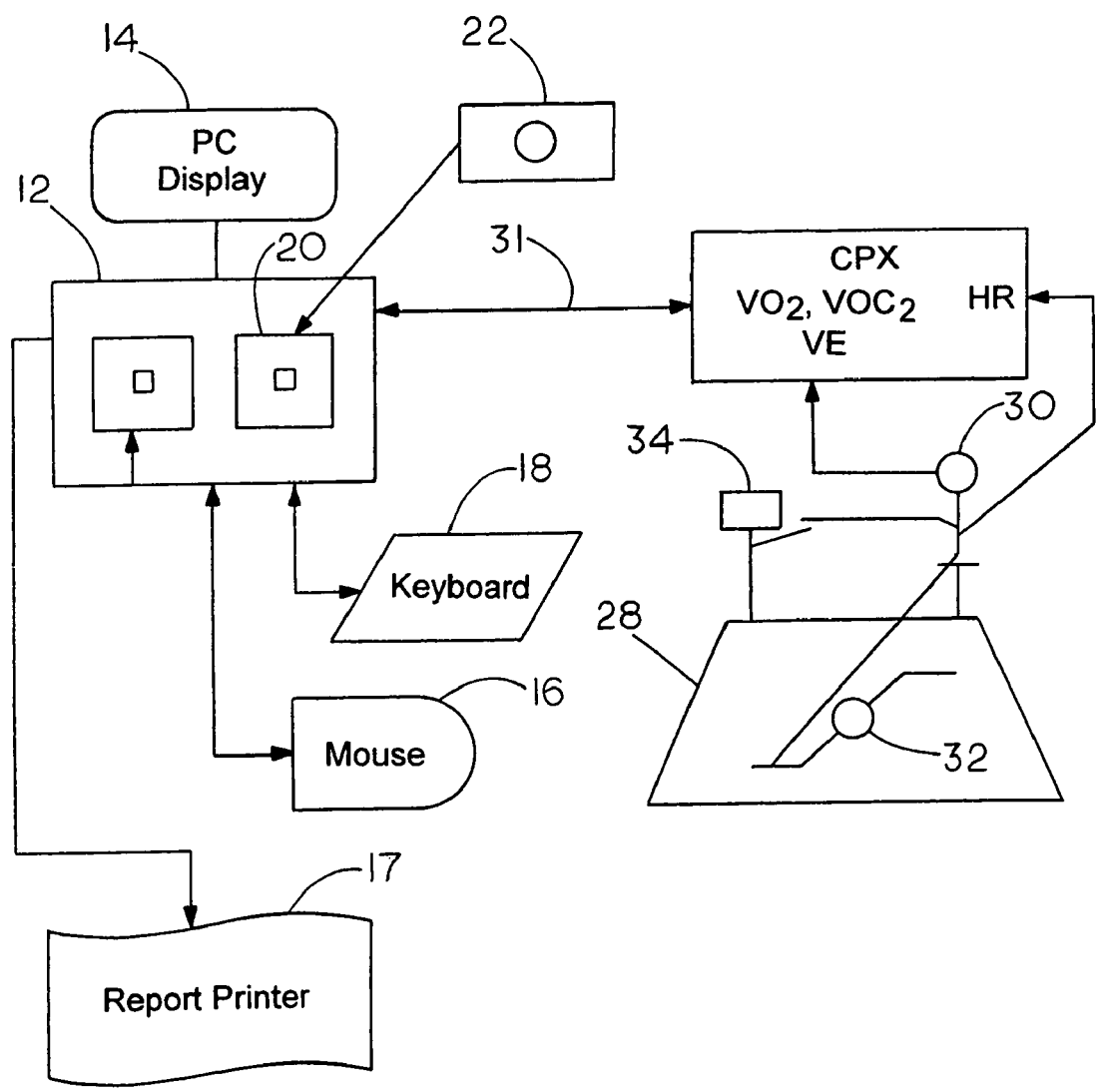
FIG. 1 is a schematic drawing that illustrates the functional components of a CPX testing system usable with the present invention.

The following detailed description with respect to patient data is intended to be exemplary of a preferred method of utilizing the concepts of the present invention and is not intended to be exhaustive or limiting in any manner with respect to similar methods and additional or other steps which might occur to those skilled in the art. The following description further utilizes illustrative examples, which are believed sufficient to convey an adequate understanding of the broader concepts to those skilled in the art, and exhaustive examples are believed unnecessary.

General Considerations—The present invention is not intended to make decisions, but rather to provide information to guide the decision making process by the physician. In doing so, decisions regarding cuff inflation pressure and cuff inflation duration can be made. In some cases, the answer to these questions may be no—there is no clear reason to use one choice over another. Even in this case, the decision making process described in the present invention is an improvement over a process devoid of specific, sensitive data. In the present invention, specificity is provided by a quantitative analysis of response variables that are based upon well known, proven measurements of human physiology. Sensitivity is supported by qualitative assessments of the measurements themselves.

The present invention also provides information that can be used to make decisions acutely (is the new cuff inflation pressure better than the last pressure?) and chronically (has patient mortality been improved as a result of the therapy?). In the latter case, factors such as chronic adaptation to exercise and therapies other than ECP may influence changes in the patient's condition. Since the general objective of all patient therapy is to improve patient outcome, the decision-making tools described in the present invention increase the likelihood that ECP will contribute to improved patient outcome.

The general class of data utilized in the present invention, dynamic-cardiopulmonary (DCP), is obtained at rest during the ECP session. Such data can be viewed as an "acute" evaluation of the primary "endpoint" to gauge the effect of ECP on hemodynamic and pulmonary performance and on left ventricular stroke volume.

The physiologic changes are measured using a cardiopulmonary exercise testing system (CPX) to measure selected variables associated with expired oxygen, carbon dioxide, ventilation, and heart rate. In theory, certain benefits derived from the present invention could be implemented using only a carbon dioxide analyzer equipped with a means for displaying the expired $CO_2$ waveform. However, because of the requirement for measuring "forward" pump function, both heart rate and oxygen consumption, per breath, are needed to measure $O_2$ Pulse. Consequently, a carbon dioxide analyzer alone is insufficient.

During the acute phase of evaluation, the dependent variables, $ETCO_2$, $EQCO_2$, $O_2$ Pulse, and the ventilatory efficiency slope, are measured during steady-state conditions at rest. In the present invention, the independent variables are 1) cuff inflation pressure (CIP), and 2) the cuff inflation duration (CID) values. Thus, changes made by the physician to an independent variable have the effect of changing the ventricular filling and stroke output of the heart that, in turn, alters the ventilation-perfusion coupling. As the local autoregulatory mechanisms seek to restore the synchronization of alveolar and pulmonary perfusion, the dependent variables rapidly change, are measured, and the measured values are automatically scaled and displayed to provide visual feedback to the physician during cuff inflation pressure and duration selection. In doing so, a physician is provided with a true, physiologic assessment of the patient's condition resulting from changes made to an independent variable at any point in time during the procedure.

The data gathering aspect of the invention involves known techniques and analyses and it is the aspects of processing, combining, and presenting the data in which the invention enables an observer to gain new and valuable insight into the present condition and condition trends in patients. Thus, in accordance with the preferred method, a dynamic cardiopulmonary analysis is displayed for each data set. The performance of such a test is well understood by individuals skilled in the art, and no further explanation of this, except for the cuff inflation pressure/duration optimization protocol, is believed necessary.

Equipment—With this in mind typical hardware is shown in FIG. 1, which illustrates typical equipment whereby a cardiopulmonary exercise test (CPX) may be conducted and the results displayed in accordance with the method of the present invention. The system is seen to include a data processing device, here shown as a personal computer of PC 12, which comprises a video display terminal 14 with associated mouse 16, report printer 17 and a keyboard 18. The system further has a floppy disc handler 20 with associated floppy disc 22. As is well known in the art, the floppy-disc handler 20 input/output interfaces comprise read/write devices for reading prerecorded information stored, deleting, adding or changing recorded information, on a machine-readable medium, i.e., a floppy disc, and for providing signals which can be considered as data or operands to be manipulated in accordance with a software program loaded into the RAM or ROM memory (not shown) included in the computing module 12.

The equipment used in the exercise protocol for the chronic assessment includes either a bicycle ergometer or treadmill designed for use in a cardiopulmonary stress testing system (CPX) as is represented at 28 together with a subject 30 operating a pedal crank input device 32 of the ergometer. A graphic display device 34 interfaces with the subject during operation of the CPX device The physiological variables may be selected from heart rate (HR), ventilation (VE), rate of oxygen uptake or consumption ($VO_2$) and carbon dioxide production ($VCO_2$) or other variables derived from these basic measurements. Physiological data collected is fed into the computing module 12 via a conductor 31, or other communication device.

Figure 2:
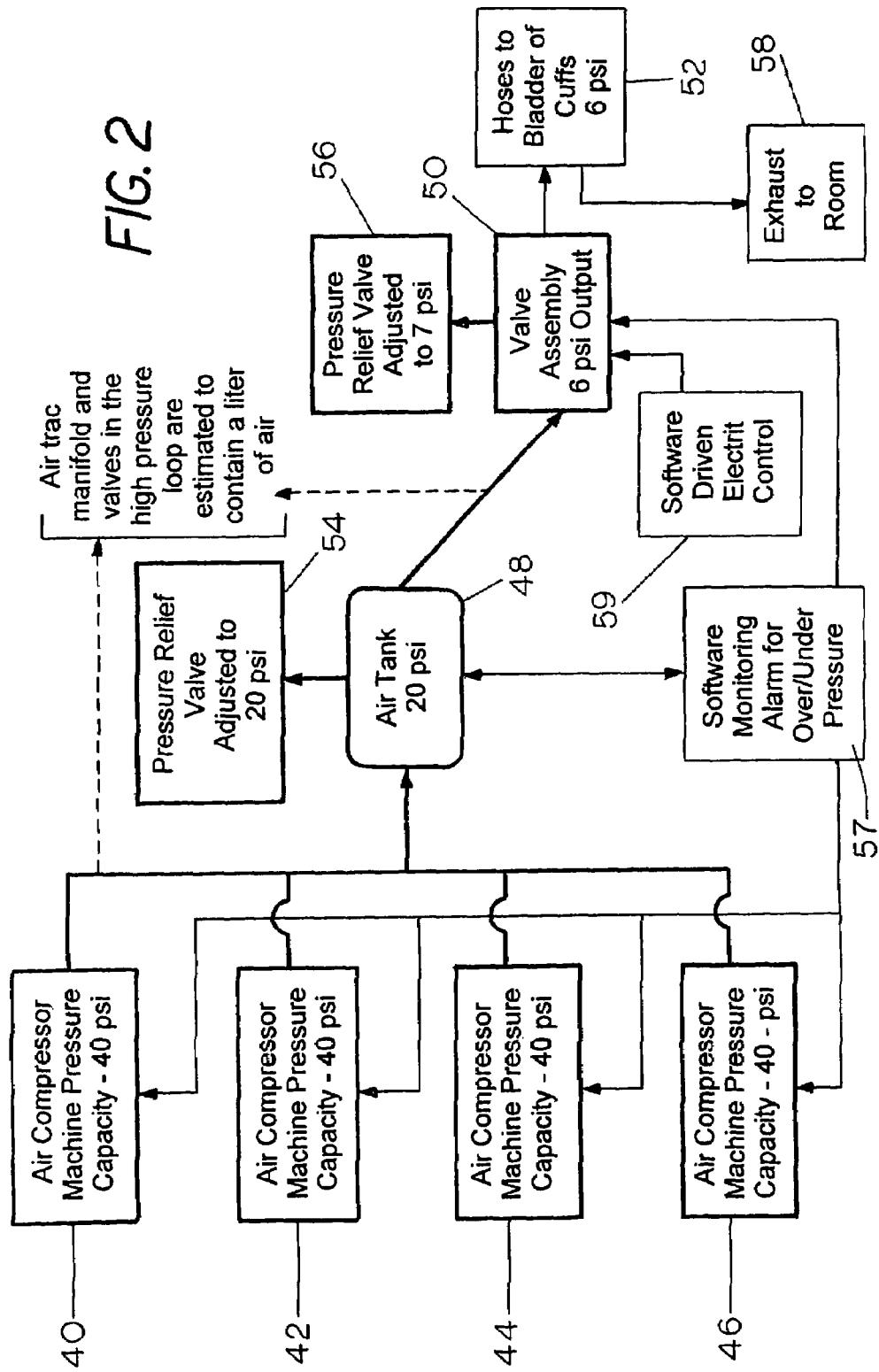
FIG. 2 is a schematic drawing that illustrates the functional components of an external counterpulsation system.

The equipment used in providing ECP therapy is schematically illustrated in FIG. 2. The equipment includes a compressor system including parallel units 40, 42, 44 and 46, which supply an air tank 48 which, in turn, supplies air to a valve assembly 50. The valve assembly 50 supplies air to hoses which are used to inflate the cuffs in accordance with the testing procedure of the invention at 52. Pressure relief is provided for the air tank by a relief valve 54 and to the valve assembly via pressure relief valve 56. The cuffs are exhausted to the room when deflated by an exhaust valve depicted by the box 58. An electronic control system as shown including connected software monitoring and alarm system 57 and electronic valve control 59.

It should be noted that either a PC (12) or the ECP microcontroller (50) could be used to acquire the measurements and process those measurements to implement the present invention. Therefore, the further detailed description of the present invention will be made independent of the type and characteristics of the data processing means.

Figure 3:
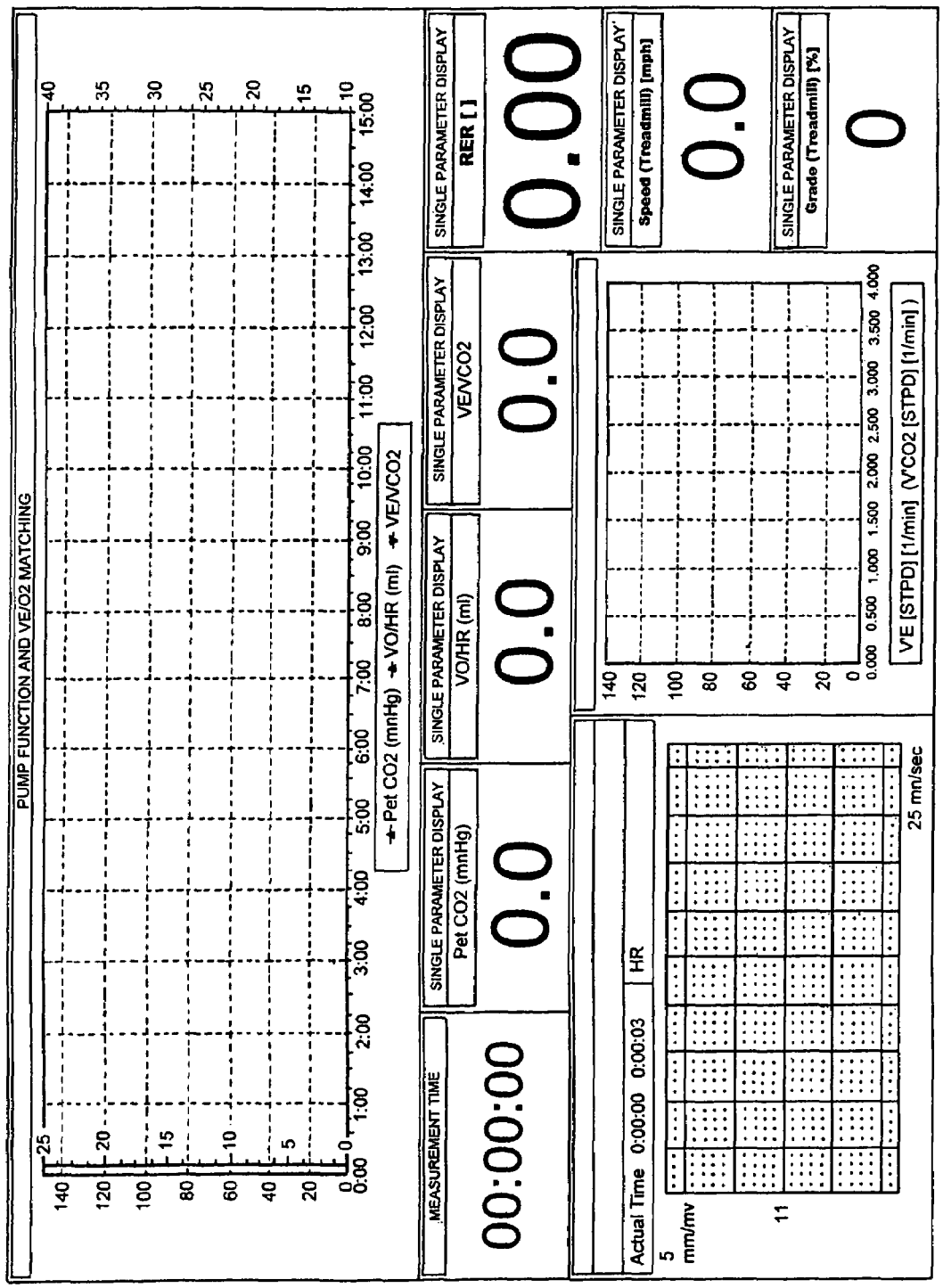
FIG. 3 illustrates the data display viewed by the physician while acquiring data using the present invention.

Acute Assessment—Optimal Cuff Inflation Pressure and Duration During ECP Therapy The present invention provides a feedback mechanism to gauge the effectiveness of the choices for cuff inflation pressure and duration settings. Since the main objective of ECP therapy itself is improved hemodynamic and pulmonary performance, the present invention provides a direct measurement of hemodynamic and pulmonary performance that can be used in real-time to evaluate if the choices are optimally reached. This can be determined on a relative basis for different inflation pressures and duration factors using a display of these variables as shown in FIG. 3 Variable Display.

The present invention further provides a computer assisted optimizing process for optimizing cuff inflation pressures and duration of pressurization of the cuffs located on the patient. An "acute assessment" of any combination of cuff inflation pressure and duration that can be programmed is obtained by monitoring of parameters indicative of the patient's forward pump function or stroke volume output, as well as retrograde effects on filling pressures, pulmonary venous flow, and gas exchange at the alveolar/capillary membrane interface. The best choices are $O_2$ Pulse for "forward" pump function and $EQCO_2$ for "retrograde" effects. However, in order to further refine the selection process, additional measurements such as the linear ventilatory efficiency slope [Minute Ventilation (VE) to expired Carbon Dioxide ($VCO_2$) slope] and $ETCO_2$ can be included. The most optimally programmed cuff inflation pressure and duration will result in the highest expired $ETCO_2$ and $O_2$ Pulse values and the best ventilation efficiency (lowest linear slope) and lowest $EQCO_2$ during ECP therapy.

These parameters are measured at pre-determined values for cuff inflation pressure and duration, as defined in the table identified in FIG. 4 as Boundary Conditions. A unique table of Boundary Conditions is established for each manufacturer of ECP systems, and the size of the table, in terms of number of rows and number of columns, can be adjusted to accommodate many different such devices. In the example provided in FIG. 4, three values of cuff inflation pressure (CIP) are stored that correspond to minimum 60, average 62, and maximum 64 pressure values allowable by the ECP system. Similarly, three values of cuff inflation duration (CID) are stored that correspond to the minimum 66, average 68, and maximum 70 duration values allowable by the ECP system. To expedite the procedure, the data collection phase is divided into two sessions of 4.5-6 minute sessions while the patient is undergoing ECP therapy (FIG. 5—Optimization Protocol). In the example provided in FIG. 5, during the first 4.5 minutes, the three values of cuff inflation duration are sequentially programmed into the ECP controller every 1.5 minutes. This programming can be accomplished manually or automatically. After zeroing all entries, all measured data for each breath during the 1.5-minute collection period associated with each of the three cuff inflation duration values is stored into the tables at 82 in FIG. 6.

Figure 7:
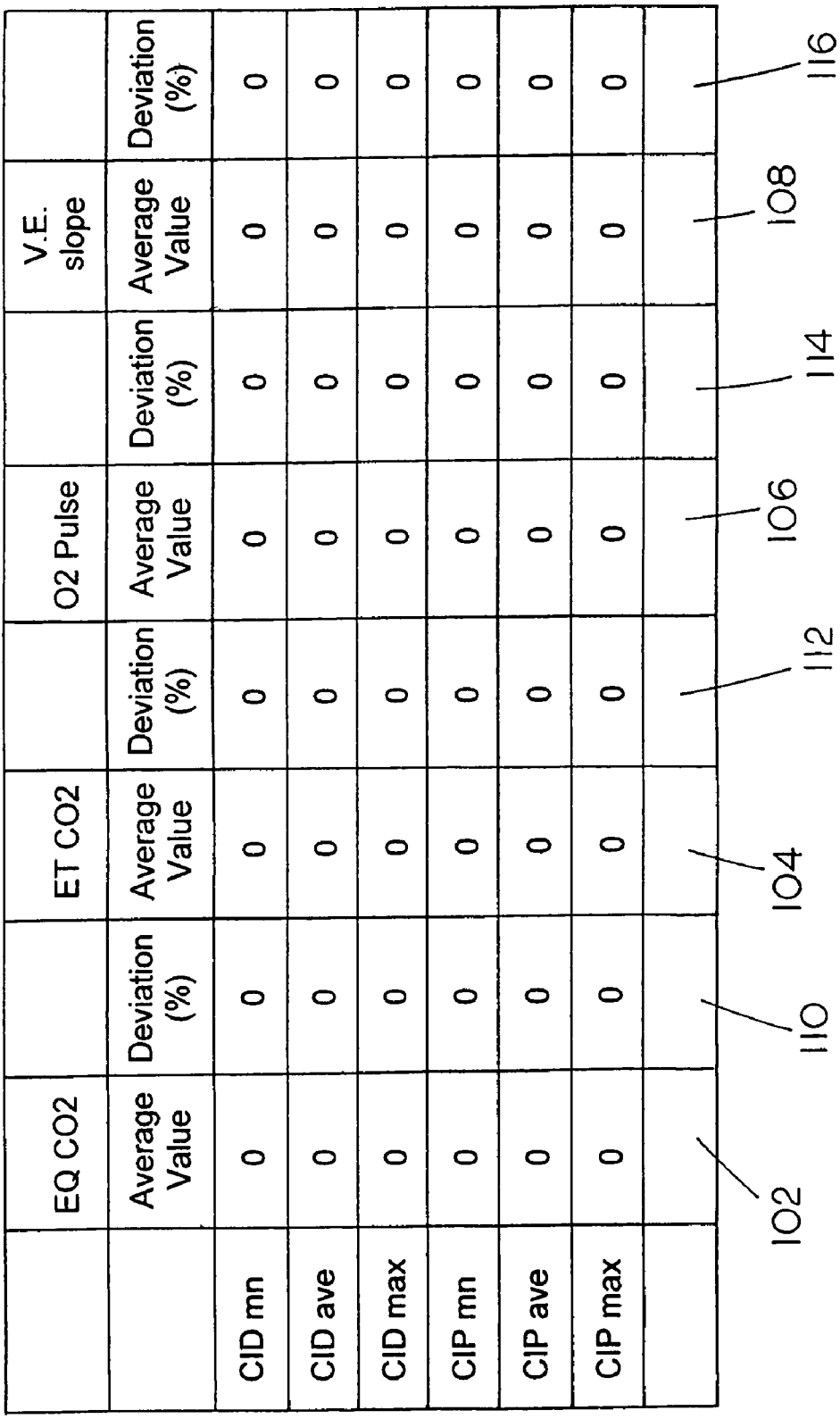
FIG. 7 illustrates the organization of Intermediate Data after each 1.5 minute segment of the Optimization Protocol.

Upon completion of each of the 1.5-minute data collection periods, the central tendency and deviation percentage of each measured variable is computed and, after zeroing all entries, stored in an Intermediate Table as described in FIG. 7. Only data for breaths recorded during the last one minute of each collection period is used in the calculations. Such computations of central tendency can include, but is not limited to, the simple arithmetic average, as at 102, 104, 106 and 108 in FIG. 7 for example. The Deviation % is as in 110, 112, 114, and 116 is first calculated by summing, for each breath in the one-minute calculation period, the absolute value of the difference between the average value 102 and the recorded value. This total is then divided by the product of the number of breaths in the calculation period times the average value. Multiplying this calculation by 100 yields the Deviation %. The Deviation % is intended to provide a qualitative assessment of the "tightness" of the data sets. In other words, a small Deviation % is indicative of low variability of the data in each set, hence a high quality test. A large value of Deviation % would indicate unwanted patient events (coughing, for example) or unwanted physiologic consequences (Cheyne-Stoke breathing patterns, for example)

Upon completion of the first 4.5 minutes of data collection, further processing of the data stored in the Intermediate Table is performed. The Decision Matrix as in the example shown in FIG. 8 is first zeroed, and the following steps are taken to calculate the values for each row and column.

Step 1—Assign Rank—The Rank value is intended to provide a qualitative assessment of the optimal choice for either cuff inflation pressure or cuff inflation duration. First, the highest average value for $O_2$ Pulse and $ETCO_2$ and the lowest average value for $EQCO_2$ and V.E. slope are identified. A Rank value of 100 is assigned to the corresponding position in the Decision Matrix for each such determination. For example, if the highest value found in column 2, rows 3-5, in FIG. 7 was at row 4, or CID ave, then 100 is assigned in FIG. 8 to column 2 in the row defined as CID ave. The associated value for Deviation % found in FIG. 7 is also stored in the next column in the same row of FIG. 8. Next, the lowest average value for $O_2$ Pulse and $ETCO_2$ and the highest average value for $EQCO_2$ and V.E. slope are identified. A Rank value of 50 is assigned to the corresponding position in the Decision Matrix for each such determination. For example, if the lowest-value found in column 2, rows 3-5, in FIG. 7 was at row 5, or CID max, then 50 is assigned in FIG. 8 to column 2 in the row defined as CID max. The associated value for Deviation % found in FIG. 7 is also stored in the next column in the same row of FIG. 8. A Rank value of 75 is then assigned to the Rank column in the row for which no entry has been previously made, and the associated value for Deviation % found in FIG. 7 is also stored in the next column is the same row of FIG. 8. In this manner entries will have been made in all columns for the rows identified as CID min, CID ave, and CID max except the S % column and the Average of the Totals.

The next step is to compute, for each row in FIG. 8 identified as CID min, CID ave, and CID max, the Average Total Rank. This is done by summing the individually assigned Rank values for each of the variables in the same row and dividing by 4. The "perfect" Average Rank, then, is 100, which indicates that each variable for that particular setting is in theoretical conformance—the two that should be the highest are the highest and the two that should be the lowest are the lowest.

Step 2 Define Deviation—Similarly, the Average Deviation Percentage is calculated for each such row and stored in the column of that row identified in FIG. 8 as D %.

Step 3—Define Separation—The next step is to compute the values for Separation % for each of the rows in FIG. 8 identified as CID min, CID ave, and CID max. The Separation % value provides a qualitative assessment of the difference, or separation, between the components of Rank (in this example, average value of the variable data set at each CID setting). A small value of S % indicates that there is little measured difference between the average values of data sets at each duration setting; hence the test may prove inconclusive. The higher the value of S %, the more conclusive the test results. For each of the columns for each of the variables, a value of 0 is assigned to the S % column in the row having the maximum average Rank. For example, in FIG. 8, the row with the highest average Rank, 93.75, is the row CID ave, consequently, each column identified as S % is set to 0. The values for S % for each column of the remaining, unassigned rows is first computed by subtracting the average value from FIG. 7 for the associated row from the average value from FIG. 7 for the row that has been assigned a value of 0 for S %. The absolute value of this operation is then divided by the average value from FIG. 7 for the row that has been assigned a value of 0 for S %. Multiplying this operation by 100 yields S % for each of the remaining 2 rows, in this example, for each variable. In a similar fashion described to compute average Rank and D %, average S % is computed for each row and stored in the S % column under Average of Totals.

Figure 9:
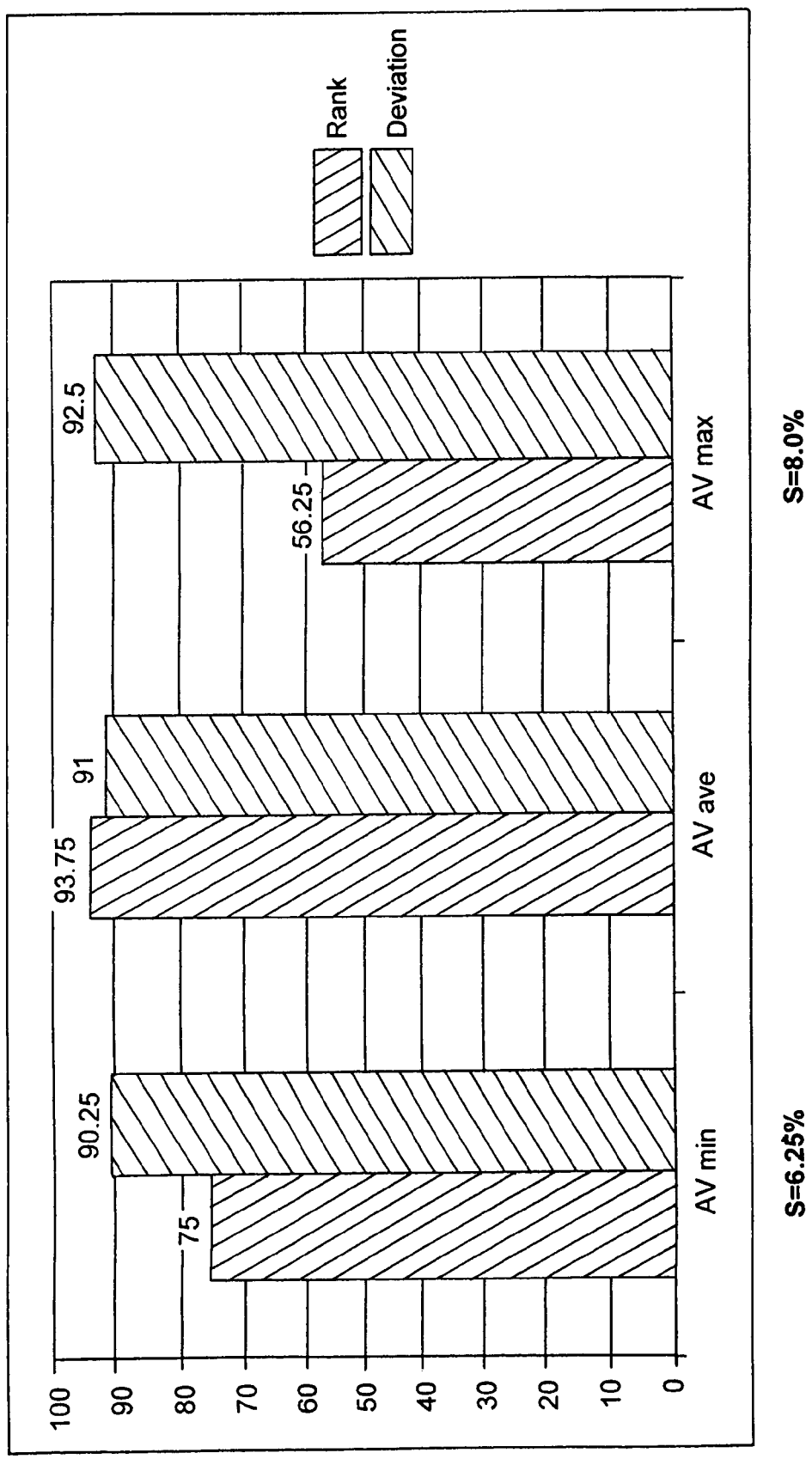
FIG. 9 illustrates a Report Summary in a histogram format for the data used in FIG. 8.

The physician then prints the final report for review at 90 in FIG. 5. The final report consists of a printed version of the Decision Matrix FIG. 8 and a Report Summary, FIG. 9, summarizing the calculations stored in the Decision Matrix in the form of a histogram in this case (any other choice for graphical display is suitable). The Rank bar for each CID setting is placed on a scale with a maximum value of 100. The height of the bar for each setting is then the value of Average Rank from the Decision Matrix for that setting. To match the "bigger is better" assumption for Rank value, the height of the D % bar in FIG. 9 is scaled to a value equal to 100 minus the average D % for each setting. The average S % for the settings with lower average Rank values is printed below their associated setting columns. Thus, the optimal setting is quantified as the setting with the highest average Rank, and this, in turn, can be assessed qualitatively by the relative heights of the Rank columns (equal heights indicate poor quality), average Deviation % (large values indicates poor quality), and Separation % (low value indicates poor quality). During a one-minute (or optionally, longer) period, the physician selects and programs the CID value at 92 in FIG. 5 after first inspecting the Decision Matrix FIG. 8 and the Report Summary FIG. 9.

The second 4.5 minute data collection phase is started. Similarly, each of the CIP values defined in the Boundary Conditions Table FIG. 4 are programmed every 1.5 minutes and each of the measured values for each breath is stored into the Stored Data Sets (84) identified in FIG. 6. The entire process described above for selecting CID is repeated in detail for selecting CIP, using instead those rows identified in FIGS. 6, 7, and 8 for CIP data storage. After inspecting the Decision Matrix FIG. 8 and the Report Summary FIG. 9 (in this case, showing CIP min, CIP ave, and CIP max), the physician then selects and programs the CIP value at 96 in FIG. 5.

Upon completion of the acute phase of evaluation, the patient is ready for the chronic assessment phase, which may be performed immediately after the acute assessment or at a later time.

The invention has been described in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as the equipment details and operating procedures can be accomplished without departing from the scope of the invention itself.

The invention claimed is:

1. A method of optimizing external counterpulsation therapy (ECP) provided to a patient with heart disease including:
   (a) non-invasively measuring hemodynamic and pulmonary performance in terms of one or more variables selected from the group consisting of forward pump function or stroke volume output, retrograde effects on filling pressures, pulmonary venous flow, and gas exchange at the alveolar/capillary membrane interface while the patient is at rest and connected to an ECP device;
   (b) displaying non-invasive cardiopulmonary gas exchange variables; and storing said non-invasive cardiopulmonary gas exchange variables as data sets, each set being associated with a unique value of cuff inflation duration (CID) and cuff inflation pressure (CIP); and
   (c) utilizing the stored cardiopulmonary gas exchange variable sets in selecting an optimal combination of CID and CIP values from several possible such values uniquely for individual patients.

2. A method as in claim 1 wherein forward pump function of the heart is selectively derived from oxygen pulse ($VO_2$/HR), and retrograde effects on filling pressures, pulmonary venous flow, and gas exchange at the alveolar/capillary membrane interface are selectively derived from the ventilatory equivalent for $CO_2$ ($VE/VCO_2$).

3. A method as in claim 2 including the step of utilizing additional cardiopulmonary gas exchange variables selected from the group consisting of end tidal $CO_2$ ($ETCO_2$) and the ventilatory efficiency slope.

4. A method as in claim 3 wherein the values for CID and CIP are defined in a boundary conditions table unique to an ECP manufacturer of interest.

5. A method as in claim 2 wherein the values for CID and CIP are defined in a boundary conditions table unique to an ECP manufacturer of interest.

6. A method as in claim 1 including the step of measuring retrograde effects using an end-tidal CO2 analyzer.

7. A method of optimizing external counterpulsation therapy (ECP) provided to a patient with heart disease while the patient is at rest and connected to an ECP device including:
   (a) non-invasively measuring hemodynamic and pulmonary performance in terms of one or more variables selected from the group consisting of forward pump function or stroke volume output, retrograde effects on filling pressures, pulmonary venous flow, and gas exchange at the alveolar/capillary membrane interface wherein forward pump function of the heart is selectively derived from the oxygen pulse ($VO_2$/HR), and retrograde effects on filling pressures, pulmonary venous flow, and gas exchange at the alveolar/capillary membrane interface are selectively derived from the ventilatory equivalent for $CO_2$ ($VE/VCO_2$);
   (b) displaying non-invasive cardiopulmonary gas exchange exercise variables; and storing said non-invasive cardiopulmonary gas exchange variables as data sets, each set being associated with a unique value of cuff inflation duration (CID) and cuff inflation pressure (CIP)
   (c) utilizing the stored cardiopulmonary variable sets to assist a physician in selecting the optimal combination of CID and CIP values from several possible such values uniquely for individual patients;
   (d) wherein the selection process includes:
      (1) executing a CID/CIP optimization protocol defining the time schedule for system operator tasks and data processing tasks for each unique value of CID and CIP as defined in (2);
      (2) storing variable values measured for each breath during the optimization protocol as in (1) into a stored data sets table for subsequent analysis;
      (3) computing and storing a central tendency and a percent deviation from the central tendency for each measured variable in each set obtained immediately after collection in (2) into an Intermediate table for subsequent analysis;
      (4) computing and storing into a decision matrix ranking values for quantifying the response to changes in CID and CIP settings using the values obtained in (3);
      (5) computing and storing into a decision matrix deviation indices to provide a qualitative assessment of the variability of the data sets used to compute the ranking values obtained in (4)
      (6) computing and storing into a decision matrix separation indices to provide a qualitative assessment of the magnitude of the difference between the central tendencies of the data sets used to calculate the ranking values in (4);
      (7) selectively printing a report of the decision matrix with all values used to compute average rank, deviation, and separation in (4), (5), and (6); and
      (8) selectively printing a graphical report in the form of a histogram with two bars—one bar representing the ranking values determined in (4) the other bar representing the average deviation % computed from (5)—and the separation indices computed in (6).

8. A method as in claim 7 wherein the variables computed in steps (1) to (6) are represented in common graphical formats selected from the group consisting of lines, bars, and pie charts.

9. A method as in claim 7 wherein variables are measured under resting, steady-state conditions and are treated as dependent variables for assessments, and independent variables are cuff inflation duration and cuff inflation pressure.

10. A method as in claim 7 wherein decisions can be made from selected quantitative and qualitative information.

11. A method of optimizing external counterpulsation therapy (ECP) provided to a patient with heart disease including:
   (a) non-invasively measuring hemodynamic and pulmonary performance in terms of one or more variables selected from the group consisting of forward pump function or stroke volume output, retrograde effects on filling pressures, pulmonary venous flow, and gas exchange at the alveolar/capillary membrane interface wherein forward pump function of the heart is selectively derived from the oxygen pulse ($VO_2$/HR), and retrograde effects on filling pressures, pulmonary venous flow, and gas exchange at the alveolar/capillary membrane interface are selectively derived from the ventilatory equivalent for $CO_2$ ($VE/VCO_2$);
   (b) utilizing additional cardiopulmonary variables selected from the group consisting of end tidal $CO_2$ ($ETCO_2$) and the respiratory drive (VT/Ti);
   (c) displaying non-invasive cardiopulmonary gas exchange variables; and storing said non-invasive cardiopulmonary gas exchange variables as data sets, each set being associated with a unique value of cuff inflation duration (CID) and cuff inflation pressure (CIP)

(d) utilizing the stored cardiopulmonary variable sets to assist a physician in selecting the optimal combination of CID and CIP values from several possible such values uniquely for individual patients; wherein
(e) the selection process includes:
 (1) executing a CID/CIP optimization protocol defining the time schedule for system operator tasks and data processing tasks for each unique value of CID and CIP as defined in claim (3);
 (2) storing variable values measured for each breath during the optimization protocol as in (1) into a stored data sets table for subsequent analysis;
 (3) computing and storing a central tendency and a percent deviation from the central tendency for each measured variable in each set obtained immediately after collection in (2) into an Intermediate table for subsequent analysis;
 (4) computing and storing into a decision matrix ranking values for quantifying the response to changes in CID and CIP settings using the values obtained in (3);
 (5) computing and storing into a decision matrix deviation indices to provide a qualitative assessment of the variability of the data sets used to compute the ranking values obtained in (4)
 (6) computing and storing into a decision matrix separation indices to provide a qualitative assessment of the magnitude of the difference between the central tendencies of the data sets used to calculate the ranking values in (4);
 (7) selectively printing a report of the decision matrix with all values used to compute average rank, deviation, and separation in (4), (5), and (6); and
 (8) selectively printing a graphical report in the form of a histogram with two bars—one bar representing the ranking values determined in (4), the other bar representing the average deviation % computed from (5)—and the separation indices computed in (6).

12. A method as in claim 11 wherein the variables computed in steps (1) to (6) are represented in common graphical formats selected from the group consisting of lines, bars, pie charts.

13. A method as in claim 11 wherein variables are measured under resting, steady-state conditions and are treated as dependent variables for assessments, and independent variables are cuff inflation duration and cuff inflation pressure.

14. A method as in claim 11 wherein decisions can be made from selected quantitative and qualitative information.

\* \* \* \* \*